(12) United States Patent
Liang et al.

(10) Patent No.: US 6,329,349 B1
(45) Date of Patent: Dec. 11, 2001

(54) METHODS FOR REDUCING ISCHEMIC INJURY OF THE HEART VIA THE SEQUENTIAL ADMINISTRATION OF MONOPHOSPHORYL LIPID A AND ADENOSINE RECEPTOR AGENTS

(75) Inventors: Bruce T. Liang, Merion Station, PA (US); Kenneth A. Jacobson, Silver Springs, MD (US)

(73) Assignees: Trustees of the University of Pennsylvania, Philadelphia, PA (US); The United States of America as represented by the Department of Health and Human Services, Washington, DC (US)

( * ) Notice: Subject to any disclaimer, the term of this patent is extended or adjusted under 35 U.S.C. 154(b) by 0 days.

(21) Appl. No.: 09/530,164

(22) PCT Filed: Oct. 23, 1998

(86) PCT No.: PCT/US98/22515

§ 371 Date: Apr. 24, 2000

§ 102(e) Date: Apr. 20, 2000

(87) PCT Pub. No.: WO99/20284

PCT Pub. Date: Apr. 29, 1999

Related U.S. Application Data

(60) Provisional application No. 60/062,737, filed on Oct. 23, 1997.

(51) Int. Cl.$^7$ ............... A61K 31/70; A61K 31/715; A61K 31/44

(52) U.S. Cl. ............... 514/46; 514/54; 514/353; 514/355; 514/356; 514/921

(58) Field of Search ............... 514/54, 353, 355, 514/356, 921, 46

(56) References Cited

U.S. PATENT DOCUMENTS

| | | | |
|---|---|---|---|
| 4,870,090 | * 9/1989 | Noda et al. | 514/356 |
| 5,286,718 | * 2/1994 | Elliott | 514/54 |
| 5,354,764 | * 10/1994 | Grover et al. | 514/353 |

OTHER PUBLICATIONS

Kristyne Stambaugh, et al., "A novel cardioprotective function of adenosine $A_1$ and $A_3$ receptors during prolonged simulated ischemia", Rapid Communication, H501–H505.
Jennifer Strickler, et al., Direct Preconditioning of Cultured Check Ventricular Myocytes—Novel Functions of Cardiac Adenosine $A_{2a}$ and $A_3$ Receptors, J. Clin. Invest., vol. 98, No. 8, Oct. 1996, 1773–1779.
Bruce T. Liang, "Direct preconditioning of cardiac ventricular myocytes via adenosine $A_1$ receptor and $K_{ATP}$ cahnnel", American Physiological Society, 1996, H1769–H1777.
James M. Downey, "Ischemic Preconditioning—Nature's Own Cardioprotective Intervention", TCM vol. 2, No. 5, 1992, pp. 170–176.
Roger J. Hill, et al., "Cloning, Expression and Pharmacological Characterization of Rabbit Adenosine $A_1$ and $A_3$ Receptors", The Journal of Pharmacology and Experimental Therapeutics, vol. 280, No. 1, pp. 122–128.
Vinod H. Thourani, et al., "Adenosine $A_3$–receptor stimulation attenuates postischemic dysfunction through $K_{ATP}$ channels", American Physiological Society, 1999, pp. H228–H235.
W.Ross Stacey, et al., "Selective activation of adenosine $A_3$ receptors with $N^6$–(3–Chlorobenzyl)–5'–N–methylcarboxamidoadenosine (CB–MECA) provides cardioprotection via $K_{ATP}$ channel activation", Cardiovascular Research 40 (1998) 138–145.
James R. Parratt, Protection of the heart by ischaemic preconditioning: mechanisms and possibilites for pharmacological exploitation, TiPS, Jan. 1994, vol. 15, 19–24.
Carola Gallo–Rodriquez, et al., Structure–Activity Relationships of $N^6$–Benzyladenosine–5'–uronamides as $A^3$–Selective Adenosine Agonists, J. Med. Chem., 1994, vol. 37, No. 5, pp. 636–646.
Kenneth J. Jacobson, et al., "Functionalized Cogeners of Adenosine: Preparation of Analogues with High Affinity for $A_1$ –Adenosine Receptors", J. Chem ., Sep. 1985, vol. 28, No. 9, pp. 1341–1346.
Ji–long Jiang, et al., "6–Phenyl, 4–dihydropyridine Derivatives as Potent and Selective $A_3$ Adenosine Receptor Antagonists", J. Med. Chem., 1996, vol. 39, No. 23, pp. 4667–4675.
Hea O. Kim, "2–Substitution of $N^6$–Benzyladenosine–5'–uronamides Enhances Selectivity for $A_3$ Adenosine Receptors", J. Med. Chem., Oct. 14, 1994, pp. 3614–3621.
Pier Giovanni Baraldi, et al., "Novel $N^6$–(Substituted–phenylcarbamoyl)adenosine–5'–uronamides as Potent Agonists for $A_3$ Adenosine Receptors", J. Med. Chem., 1996, vol. 39, pp. 802–806.
Suhaib M. Siddiqi, et al., "Comparative Molecular Field Analysis of Selective $A_3$ Adenosine Receptor Agonists", Bioorganic & Medical Chemistry, 1995, vol. 3, No. pp. 1331–1343.
Philip J.M. Van Galen, et al., "A Binding Site Model and Structure–Activity Relationships for the Rat $A_3$ Adenosine Receptor", Molecular Pharmacology, 1994, 45: 1101–1111.
Kenneth A. Jacobson, et al., "8–(3–Chlorostyryl)caffeine (CSC) is a selective $A_2$ –adenosine Antagonist in vitro and in vivo", FEBS Letters, May 1993, vol. 232, No. 1,2, pp. 141–144.
Kenneth A. Jacobson, "Structure–Activity Relationships of 8–Styrylzanthines as $A_2$–Selective Adenosine Antagonists", J. Med. Chem., 1993, vol. 36, pp. 1333–1342.
Kenneth A. Jacobson, et al., "$A_3$–adenosine receptors: design of selective ligands and therapeutic prospects", Drugs of the Future 1995, 20(7): 689–699.

* cited by examiner

Primary Examiner—Kevin E. Weddington
(74) Attorney, Agent, or Firm—Dann, Dorfman, Herrell and Skillman

(57) ABSTRACT

Materials and methods for reducing or preventing ischemic damage of the heart are disclosed. A preferred embodiment of the invention comprises methods of sequential administration of a plurality of cardioprotective agents to patients suffering from ischernic damage or at risk for the same.

30 Claims, 10 Drawing Sheets ously throughout all of these periods. The protocols
METHODS FOR REDUCING ISCHEMIC INJURY OF THE HEART VIA THE SEQUENTIAL ADMINISTRATION OF MONOPHOSPHORYL LIPID A AND ADENOSINE RECEPTOR AGENTS This application is a provisional of No. 60/062,737 filed Oct. 23, 1997.

Pursuant to 35 U.S.C. §202(c) it is acknowledged that the U.S. Government has certain rights in the invention described herein, which was made in part with funds from the National Institutes of Health, Grant Number HL48225.

FIELD OF THE INVENTION

The present invention relates to methods for administering compounds to protect the heart from ischemic injury. More specifically, the invention provides a novel combination of agents which act synergistically to potentiate their individual cardioprotective effects and thereby render the myocardium more resistant to ischemia.

BACKGROUND OF THE INVENTION

Several publications are referenced in this application by numerals in parentheses in order to more fully describe the state of the art to which this invention pertains. Full citations for these references are found at the end of the specification. The disclosure of each of these publications is incorporated by reference herein.

Ischemic preconditioning functions as an endogenous protective mechanism which enhances the ability of myocardium to withstand injury from prologed ischemia. Transient ischemic events, which are sufficiently brief to avoid irreversibly damaging myocardium, initiate unidentified biochemical events which limit infarct size and the occurrence of reperfusion arrhythmias following prolonged myocardial ischemias (5).

A series of studies have shown that it is possible to induce ischemic preconditioning with a variety of pharmacological agents. Adenosine is released in large amounts during myocardial ischemia and mediates potentially important protective functions in the cardiovascular system (1,4,5,7,9,14,17, 18,19,25). Adenosine can precondition the heart with reduction in the size of myocardial infarction (4,5,9,14,17, 18). Intracoronary administration of adenosine during reperfusion following prolonged no-flow ischemia can also limit infarct size in the intact heart (1, 19).

Previous studies have shown that adenosine $A_1$ and $A_3$ receptor agonists can precondition the heart when administered before the onset of ischemia (4, 5, 9, 14, 17, 18). Other studies have shown that adenosine $A_{2a}$ receptor antagonists also enhance the cardioprotective effect of preconditioning (23). These agents effectively 1) reduce infarct size; and 2) improve left ventricular function when given during reperfusion (1, 19) or during both low-flow ischemia and reperfusion in isolated perfused heart (6, 21, 22).

Monophosphoryl lipid A (MLA), a relatively non-toxic derivative of endotoxin, has also been found to provide cardioprotection in a variety of animal models (43–45) when administered prior to an ischemic event. The mechanism of myocardial protection mediated by MLA has not yet been definitively elucidated. Other effective pharmacological preconditioning agents include $K^+ATP$ channel openers and phorbol esters.

Intensive research efforts are currently focused on the development of agents and methods for treating and preventing cardiac diseases. The present invention is directed to such methods.

SUMMARY OF THE INVENTION

Methods are disclosed which may be used to advantage for preventing ischemic damage of the heart.

The methods of the invention entail the combined administration of a first cardioprotective agent and a second cardioprotective agent. The agents act synergistically to potentiate their individual cardioprotective effects. Agents suitable for use as a first cardioprotective agent are adenosine receptor agents, MLA or analogs or derivatives of MLA.

According to a preferred embodiment, the invention entails the administration of monophosphoryl lipid A (MLA), or a synthetic analog, or derivative thereof to a patient prior to a surgical treatment. Following MLA treatment, a second cardioprotective agent is administered that potentiates the cardioprotective effect of MLA. The second cardioprotective agent is delivered to the patient either before, during or after surgery. Alternatively, the second cardioprotective agent may be administered continuously throughout all of these periods. The protocols described above may be used for the treatment of patients at risk for ischemic damage from myocardial infarction, angina, or surgical complications.

Compounds suitable as second cardioprotective agents are adenosine, agonists at the $A_1$ and $A_3$ adenosine receptors, antagonists at the $A_{2a}$ adenosine receptor, and $K_{ATP}$ channel openers.

In an alternative embodiment, an adenosine receptor agonist is administered as the first cardioprotective agent and MLA or synthetic analogs thereof is administered as the second cardioprotective agent.

Methods of administration of the cardioprotective agents of the invention include direct perfusion of the organ during surgery and intravenous administration. Additionally, these agents may be administered to patients in solid form, e.g., tablets, in amounts effective to prevent or reduce ischemic damage to the heart.

DETAILED DESCRIPTION OF THE INVENTION

Figure 1:
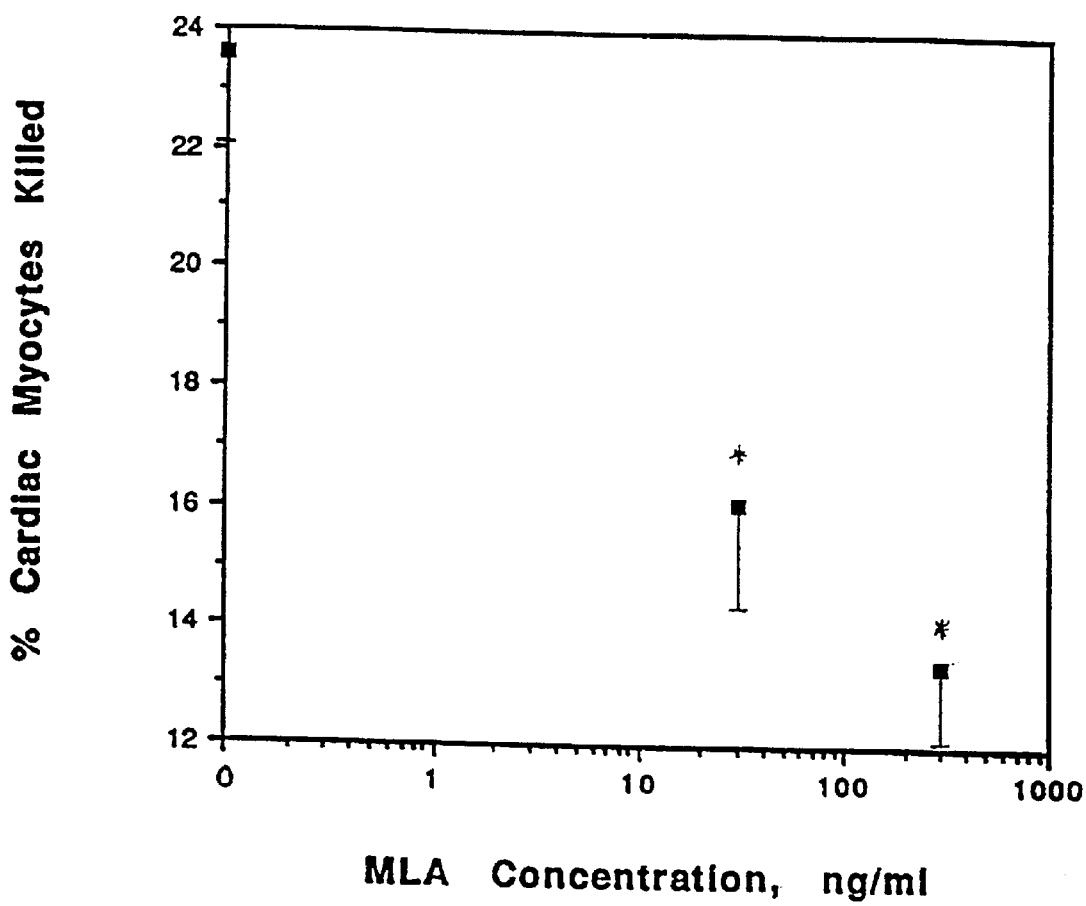
FIG. 1 is a graph showing the protective effect of pretreatment with MLA prior to prolonged ischemia in cardiac myocytes.

Preconditioning with brief ischemia before a sustained period of ischemia reduces infarct size in the perfused heart. Ventricular myocytes cultured from chick embryos retain many of the properties of the intact heart, which make them a useful model for a variety of experimental paradigms (33–39), including preconditioning (16, 23, 32). This model system has been utilized to develop novel combinations of pharmcological agents which act synergistically to treat and prevent ischemic damage of the heart.

Monophosphoryl lipid A (MLA), a derivative of the gram-negative bacterial cell wall component lipopolysaccharide A (i.e. endotoxin), induces a glibenclamide-sensitive cardioprotective effect in isolated, intact heart models of ischemia-reperfusion. The data reveal that treatment with MLA has a prolonged protective effect (31). The present invention is based on the hypothesis that MLA or MLA analogs effect cardioprotective action by enhancing the sensitivity of the cardiac myocytes to preconditioning stimuli and to cardioprotective agents. These cardioprotective agents include agonists at the $A_1$ and $A_3$ adenosine receptors, antagonists at the $A_{2a}$ adenosine receptor, $K_{ATP}$ channel openers and phorbol esters. MLA may also enhance the protective effects of these agents during prolonged, infarct-producing ischemia. These two novel cardioprotective mechanisms of MLA were investigated and the results are provided hereinbelow.

The present invention demonstrates that pretreatment of myocytes with MLA alone prior to preconditioning ischemia can enhance the cardioprotective effect of the preconditioning, thus further decreasing myocyte killing in response to an ischemic event. Furthermore, a synergistic cardioprotective effect is achieved by treatment with MLA in conjunction with adenosine, agonists of the $A_1$ and $A_3$ adenosine receptors, antagonists of the $A_{2a}$ adenosine receptor or a $K_{ATP}$ channel opening compound.

The compounds of the present invention tend to produce certain unwanted side effects when administered individually at standard dosage. Because these compounds have been discovered to act synergistically when used in combination, subthreshold concentrations may be employed in practicing the methods of the present invention. These subthreshold concentrations should induce fewer side effects and accordingly constitute an improvement in currently available methods for reducing ischemic damage to the heart.

The following definitions are provided to facilitate understanding of the present invention.

Preconditioning Ischemia

A brief ischemia which does not cause any cardiac damage, but protects the heart against damage during a subsequent prolonged ischemia. The effect of preconditioning ischemia is mediated by adenosine, which is released during the ischemia. Preconditioning may be induced by brief exposure to anoxic conditions for example.

Adenosine Receptors $A_1$, $A_3$ and $A_{2a}$ receptors are present on the myocardium (cardiac muscle cells). While activation of the $A_1$ and $A_3$ receptors is cardioprotective, activation of the $A_{2a}$ receptors is deleterious and causes damage to the cardiac muscle cells.

Stable Angina

Condition observed in certain cardiac patients having a chronic risk for myocardial ischemia because of the chronic potential for an imbalance between the supply of oxygenated blood and the demand for it. Typically, such imbalance occurs during certain stresses, such as exercise, emotional stress or stress associated with a surgical procedure.

Unstable Angina

Condition observed in cardiac patients having frequent imbalance between the supply of and the demand for oxygenated blood.

Post-myocardial Infarction Angina

Condition observed in patients who have recurrent ischemia following a heart attack.

Preconditioning Stimuli

Any drug, agent or treatment which induces preconditioning, such as brief hypoxia, adenosine, pinacidil, phorbol ester, $A_1$ or $A_3$ adenosine receptor agonists or $A_{2a}$ receptor antagonists.

Myocardial Responsiveness

The myocardium can be treated so as to enhance the effectiveness and protective effects of preconditioning. This enhancement leads to a reduction in ischemic damage.

The following methods facilitate the practice of the present invention.

Preparation of Cultured Ventricular Cells

Ventricular cells were cultured from chick embryos 14 days in ovo (Spafas Inc., Storrs, Conn.) as previously described (16, 23). Cells were cultivated in a humidified 5% $CO_2$-95% air mixture at 37 C. All experiments were performed on day 3 in culture, at which time cells exhibited rhythmic spontaneous contraction. The medium was changed to a HEPES-buffered medium containing (mM) 139 NaCl, 4.7 KCl, 0.5 $MgCl_2$, 0.9 $CaCl_2$, 5 HEPES (N-2-hydroxyethylpiperazine-N'-2-ethanesulfonic acid) and 2% fetal bovine serum, pH 7.4, 37 C. before exposing the myocytes to the various conditions at 37 C. Control myocytes were maintained in HEPES-buffered medium under room air. Hypoxia and glucose deprivation were used to induce and simulate ischemia in the cultured cells. Hypoxia was produced by placing the cells in a hypoxic incubator (NuAire) where $O_2$ was replaced by $N_2$ as previously described (16,23).

Determination of Cell Injury

The extent of hypoxia-induced injury to the ventricular cell was quantitatively determined by the percentages of cells killed. To quantitate the % of cells killed, cells were exposed to a trypsin-EDTA Hanks' balanced salt solution for 10 minutes for detachment after the various treatment, followed by centrifugation (300×g for 10 minutes) and resuspension in culture media for counting in a hemocytometer. Only live cells sedimented and the cells counted represented those that survived (46). None of the sedimented cells subsequently counted included trypan blue. In cells not exposed to hypoxia, trypsin-EDTA treatment followed by re-exposure to $Ca^{2+}$-containing culture media did not cause the appearance of trypan blue-stained cells or any significant increase in proteins or creatine kinase (CK) in the trypsin- EDTA media following the 300×g, 10 minute sedimentation of the cells. There was no protein in the culture media following a second 300×g centrifugation of resuspended cells previously treated with trypsin-EDTA. Thus, trypsin treatment, re-exposure to $Ca^{2+}$-containing media or 300×g sedimentation did not cause any significant damage to the control, normoxia-exposed cells.

The percentage of cells killed was calculated as the number of cells obtained from the control group (representing cells not subjected to any hypoxia or drug treatment) minus the number of cells from the treatment group divided by number of cells in control group multiplied by 100%.

Chemical Reagents 2-chloro-$N^6$-cyclopentyl-adenosine (CCPA) and pinacidil were purchased from Research Biochemicals International (Natick, Mass.). Phorbol 12-myristate 13-acetate (PMA) was purchased from Sigma. 8-(3-chlorostyryl)caffeine (CSC), $N^6$-(3-iodobenzyl)adenosine-5'-N-methyluronamide (IB-MECA) and 2-chloro-$N^6$-(3-iodobenzyl)adenosine-5'-N-methyluronamide (Cl-IB-MECA) were synthesized as previously described (40–42).

The following examples are provided to illustrate certain embodiments of the invention. They are not intended to limit the invention in any way.

EXAMPLE I

A cultured chick ventricular myocyte model was developed to investigate the roles of a variety of compounds known to influence preconditioning. In accordance with the present invention, it has been discovered that certain agents, when applied in combination, act synergistically to reduce ischemic damage to the heart.

Pretreatment of ventricular myocytes with MLA was assessed to determine whether it enhances the cardioprotective effect of preconditioning ischemia. Hypoxia ($O_2$ <1%) and glucose deprivation were employed to induce and simulate ischemia in the myocyte model of preconditioning (16, 23, 32).

Cardiac ventricular myocytes were cultured from chick embryos 14 days in ovo and myocyte injury was induced as described hereinbelow. MLA was added to the media at the indicated concentrations for a 4 hour period 24 hours prior to 90 minutes of simulated ischemia. The extent of myocyte injury, determined at the end of the 90 minute simulated ischemia, was assessed by the percentage of cells killed. The data represent the mean of 4 experiments. At 30 and 300 ng/ml MLA significantly lowered the percentage of cell death in response to prolonged ischemia. (One way ANOVA analysis and t test, p<0.01).

Exposure of cultured cardiac myocytes to 90 minutes of prolonged hypoxia causes cell death. FIG. 1 illustrates that prior treatment with MLA significantly reduces cell death relative to the untreated controls. These data are in agreement with the cardioprotective effect of MLA treatment seen in intact rat, rabbit, and canine hearts (43–45).

Figure 2:
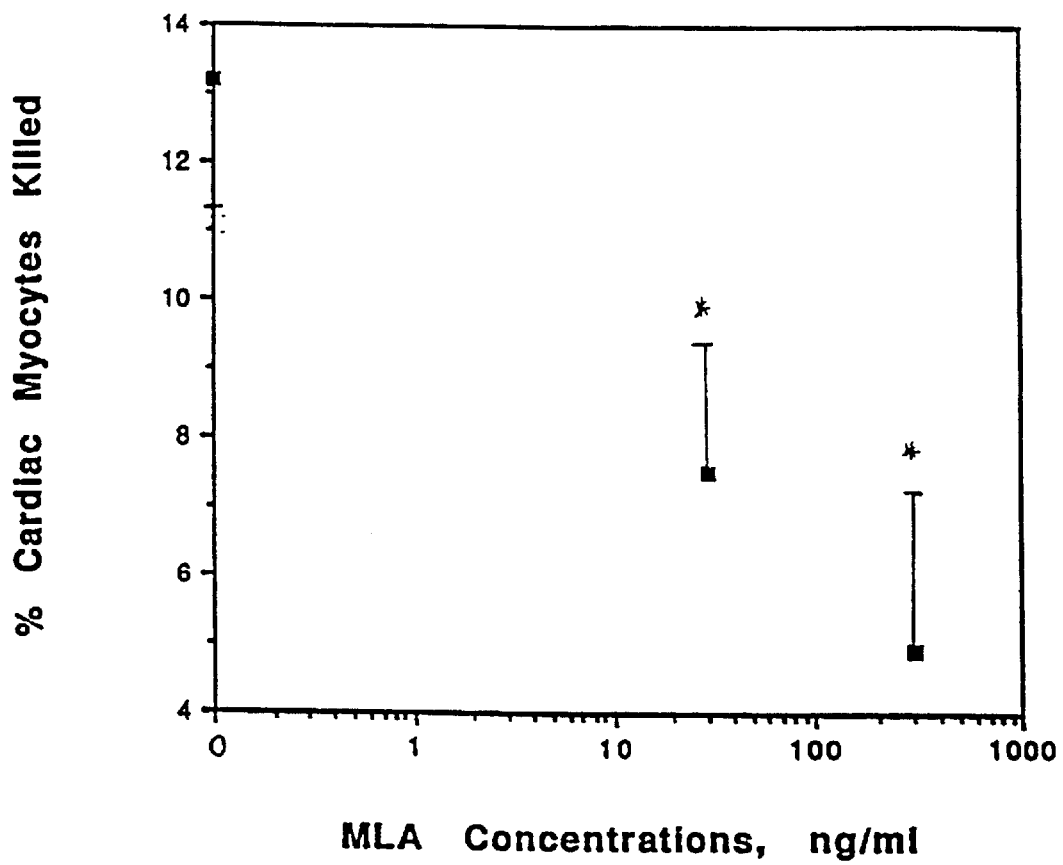
FIG. 2 is a graph showing that pretreatment with MLA enhances the cardioprotective effect of preconditioning ischemia in cardiac myocytes.

FIG. 2 shows that the extent of cardioprotection induced by a 5 minute period of preconditioning ischemia (induced by hypoxia and the absence of glucose, also termed simulated ischemia) is enhanced by pretreatment with MLA. As in FIG. 1, cultured myocytes were pretreated with the indicated concentrations of MLA for 4 hours. Twenty four hours later the cells were subjected to preconditioning ischemia, consisting of 5 minutes of simulated ischemia. After a 10 minute recovery period in normal air, the cells were subjected to a prolonged period (90 minutes) of simulated ischemia, and the percentage of cells killed was assessed. When myocytes are pretreated with MLA 24 hours prior to preconditioning ischemia treatment, there is a dose-dependent reduction in the percentage of cells killed during a prolonged ischemic event. Thus, pretreatment with MLA in combination with classic preconditioning ischemia provides a synergistic cardioprotective effect.

EXAMPLE II

Another objective of this study was the elucidation of the mechanism underlying the observed enhanced responsiveness of cardiac myocytes to preconditioning stimuli following pretreatment with MLA. The cardioprotective effects of preconditioning ischemia are mediated by adenosine receptors and the $K_{ATP}$ channel. The following experiments were performed to assess the most efficacious combination of agents for the prevention of ischemic damage to the heart.

Figure 3A:
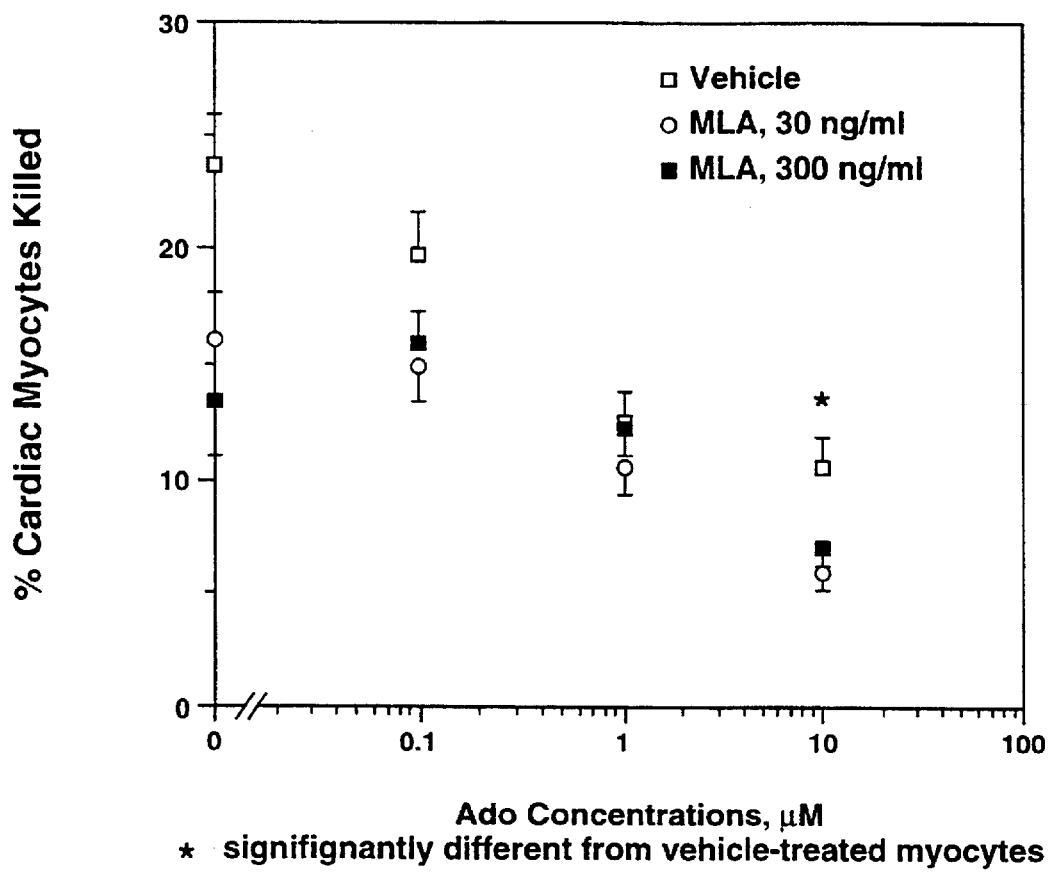
FIG. 3A is a graph showing that pretreatment with MLA enhances the preconditioning effect mediated by adenosine in cultured myocytes (□, vehicle; ○, MLA 30 ng/ml; ■, MLA, 300 ng/ml). Cardiac ventricular myocytes were subjected to classical preconditioning as described herein.
Figure 3B:
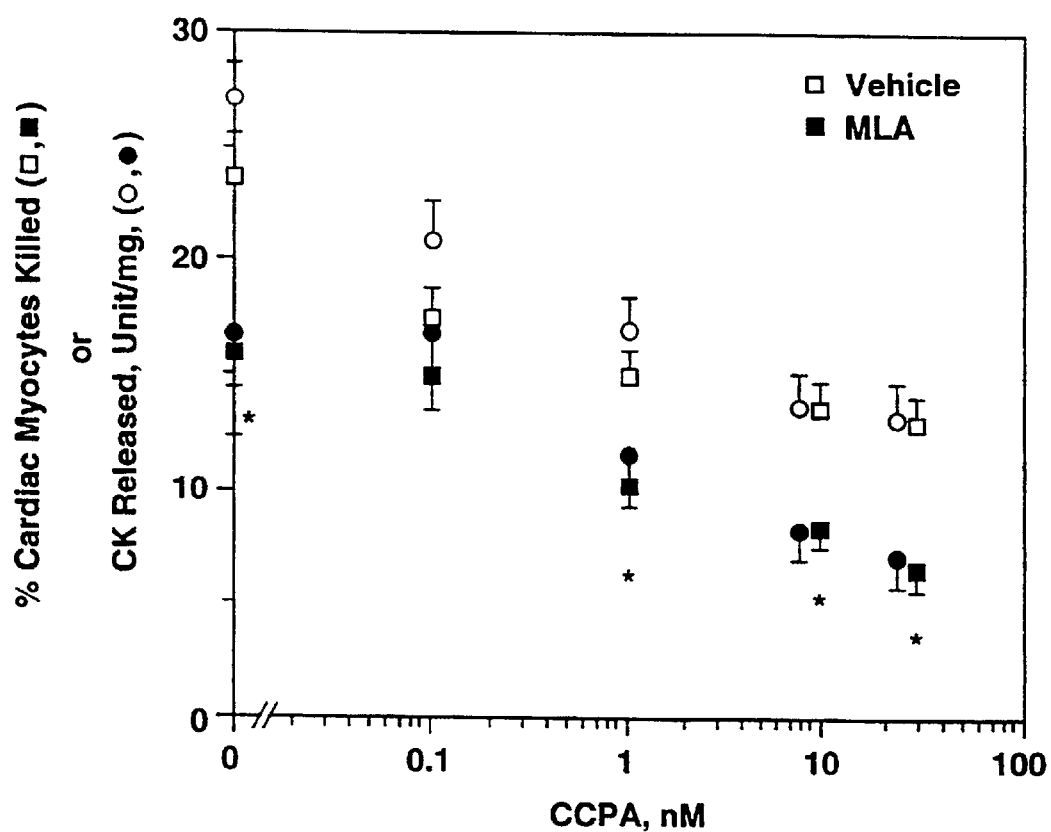
FIGS. 3B and 3C are graphs showing the results obtained when myocytes were treated with CCPA (FIG. 3B) or IB-MECA (FIG. 3C) for five minutes followed by incubation in adenosine- or agonist-free media for 10 minutes prior to 90 minutes of ischemia. Data, plotted as percentage of cells killed and the amount of CK released, represented the mean and standard error of four experiments. * indicates significant difference from vehicle-treated myocytes at the concentrations of adenosine agonists indicated (t test, P<0.001).
Figure 3C:
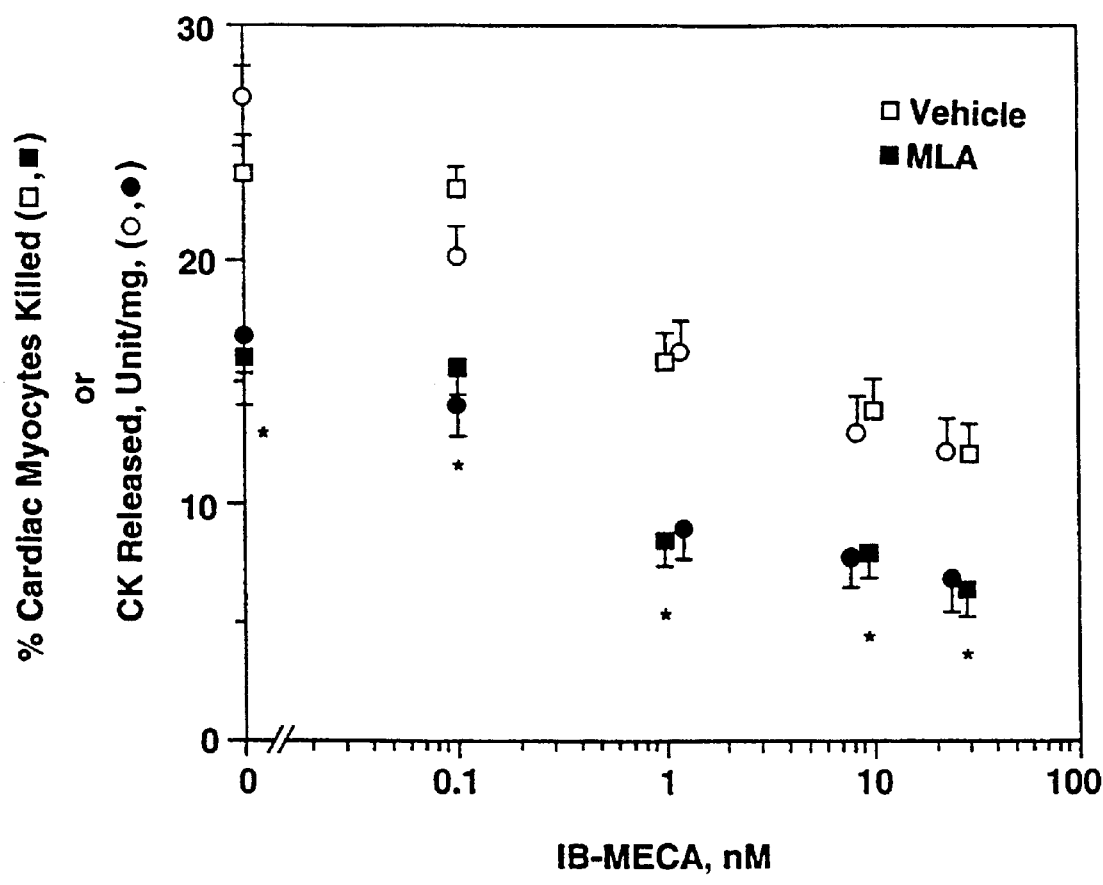

As shown in FIG. 3A, prior treatment with MLA enhanced the ability of adenosine to elicit the preconditioning response. In this experiment, myocytes were treated with either the vehicle (0.04% propylene glycol, 0.01% ethyl alcohol) or MLA 24 hours prior to a 5 minute exposure to 10 $\mu$M adenosine. Adenosine was removed by replacement of the culture medium with adenosine-free medium, and the cells were exposed to normal room air $O_2$ for 10 minutes, followed by 90 minutes of simulated ischemia treatment. The sequential treatment of myocytes with MLA followed by adenosine significantly decreased the percentage of myocytes killed by prolonged ischemia, as compared to pretreatment with the vehicle followed by exposure to adenosine. Similarly, FIGS. 3B and 3C show that prior treatment of myocytes with MLA followed by adenosine agonist, CCPA or by A3 agonist, IB-MECA, as a classical preconditioning stimuli, also significantly reduced the percentage of myocytes killed by prolonged ischemia as compared to pretreatment with the vehicle followed by exposure to CCPA or IB-MECA alone, respectively.

Figure 4:
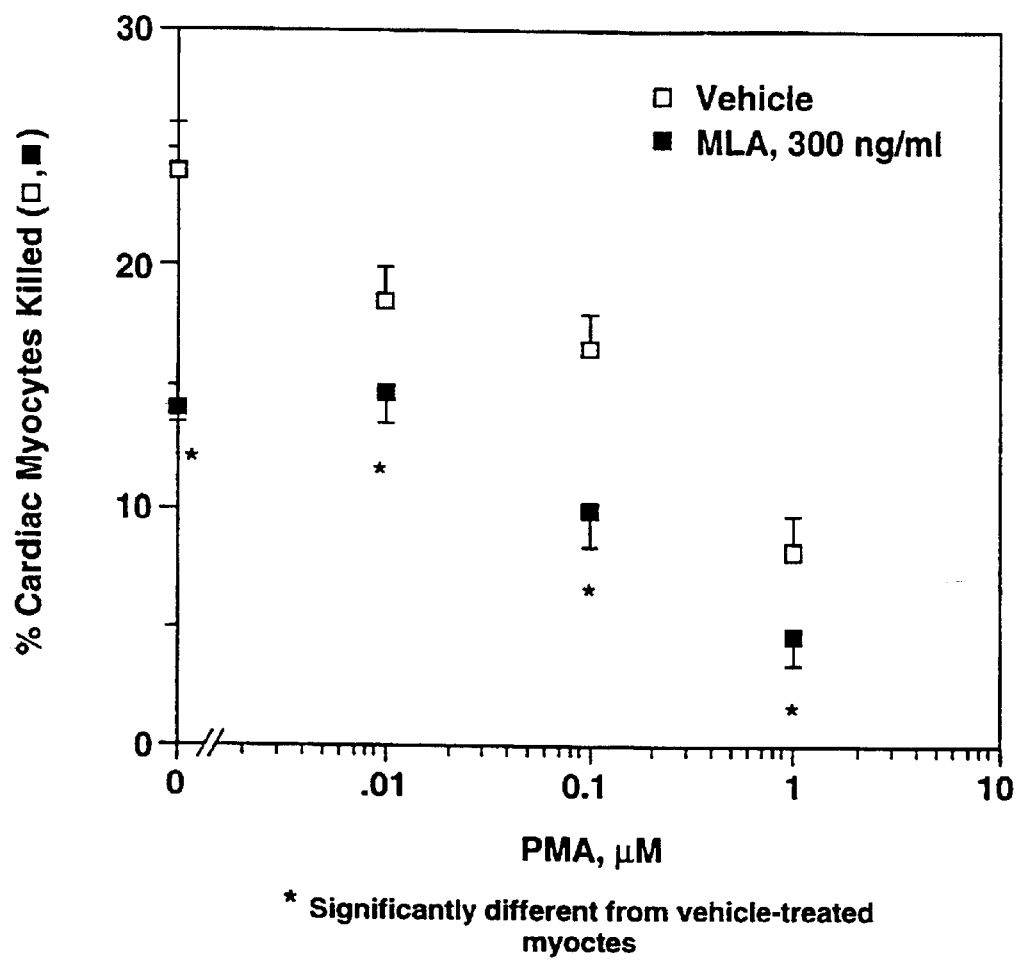
FIG. 4 is a graph showing that pretreatment with MLA enhances the preconditioning effect mediated by phorbol 12-myristate 13-acetate (PMA) (□, vehicle; ■, MLA 300 ng/ml).

An enhanced adenosine-mediated classical preconditioning response in myocytes pre-exposed to MLA suggests that MLA acts to increase the responsiveness of myocytes to the preconditioning effect of adenosine. Since the adenosine receptor mediates the preconditioning response to adenosine, such results may further suggest that MLA activates or pre-activates the adenosine receptor/G-protein/PKC/$K_{ATP}$ channel pathway. Consistent with this hypothesis, the ability of the phorbol ester phorbol 12-myristate 13-acetate (PMA) to mediate a preconditioning response was also enhanced by pretreatment with MLA. See FIG. 4. This enhancement by 300 ng/ml MLA pretreatment was significant over a range of PMA concentrations from 0.01 $\mu$M to 1 $\mu$M. The preconditioning effects of CCPA or IB-MECA were also enhanced by pretreatment of myocytes with MLA. This enhancement was not observed in myocytes pretreated with vehicle alone (data not shown).

Figure 5:
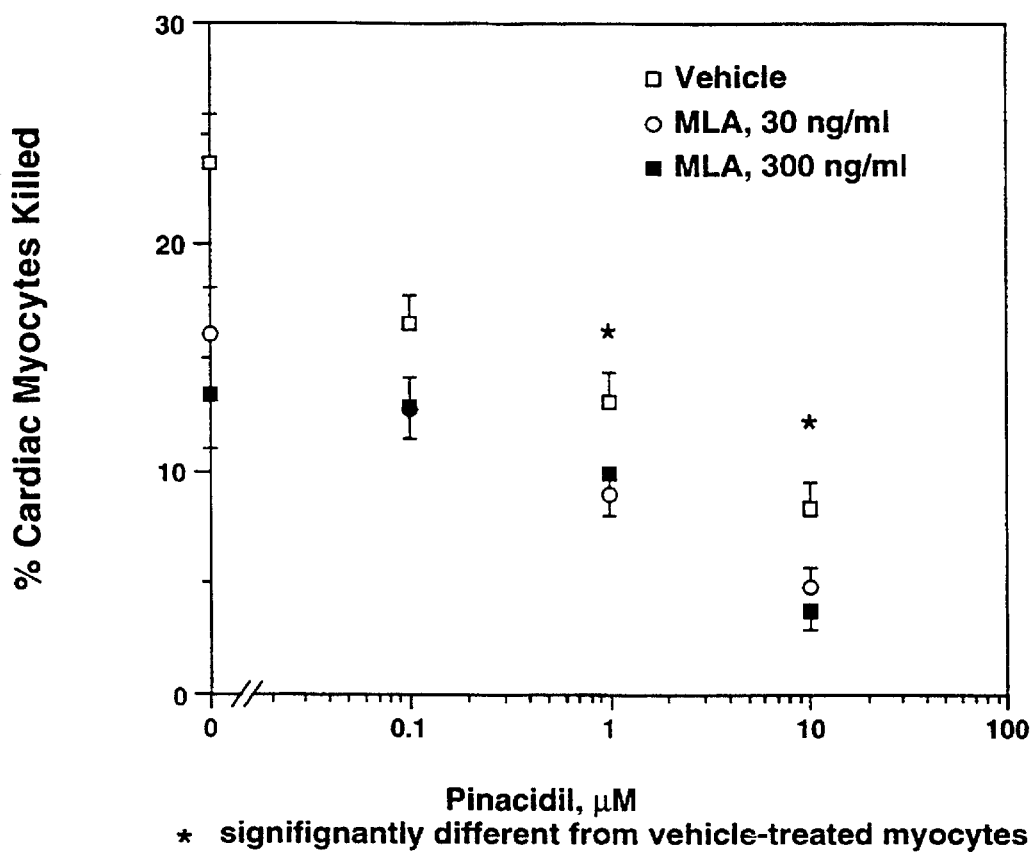
FIG. 5 is a graph showing that pretreatment with MLA enhances the preconditioning effect mediated by pinacidil in cardiac myocytes (□, vehicle; ○, MLA 30 ng/ml; ■, MLA, 300 ng/ml).

MLA pretreatment also enhanced the preconditioning response mediated by pinacidil. See FIG. 5. The data are consistent with the notion that MLA can pre-activate the adenosine receptor, G protein, PKC, the $K_{ATP}$ channel, or all four molecules. On the other hand, as the $K_{ATP}$ channel is the most distal effector of the four, MLA may pre-activate or activate the $K_{ATP}$ channel directly to render the cardiac myocyte more responsive to the preconditioning effect of the $K_{ATP}$ channel opener pinacidil.

EXAMPLE III

The experiments described in the previous examples suggest that MLA acts to enhance the preconditioning effects of various pharmacological agents such as adenosine and pinacidil.

The synergistic effects obtained using a combination of MLA and other preconditioning stimuli prompted studies assessing the activity of agonists and antagonists of adenosine receptors following pretreatment with MLA.

The experimental protocol utilized in these studies entailed pretreatment of myocytes with MLA for a 4 hour period 24 hours prior to exposure of the cardiac myocytes to 90 minutes of simulated ischemia. During this 90 minute simulated ischemia period, several cardioprotective agents were administered individually to cells and their protective effects were assessed.

Figure 6:
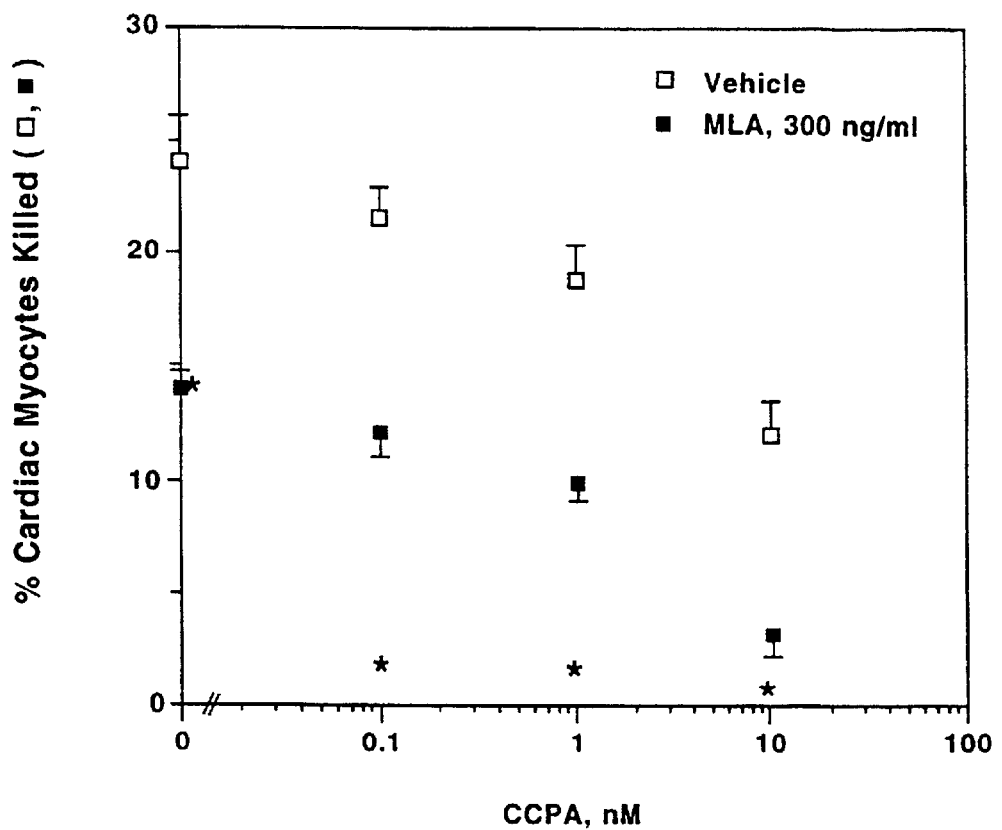
FIG. 6 is a graph showing that pretreatment with MLA enhances the cardioprotective effect of the $A_1$ adenosine receptor agonist, 2-chloro-$N^6$-cyclopentyl-adenosine (CCPA), during prolonged ischemia (□, vehicle; ■, MLA 300 ng/ml).

FIG. 6 illustrates that prior treatment of myocytes with MLA enhanced adenosine $A_1$ agonist mediated protection during the 90 minute exposure to ischemia. In MLA pretreated myocytes, the presence of CCPA during the 90 minute ischemia resulted in a greater reduction in the number of cells killed as compared to the number of cells killed following pretreatment with vehicle alone. Again the synergistic effects mediated by the two cardioprotective agents are illustrated by the data.

Figure 7:
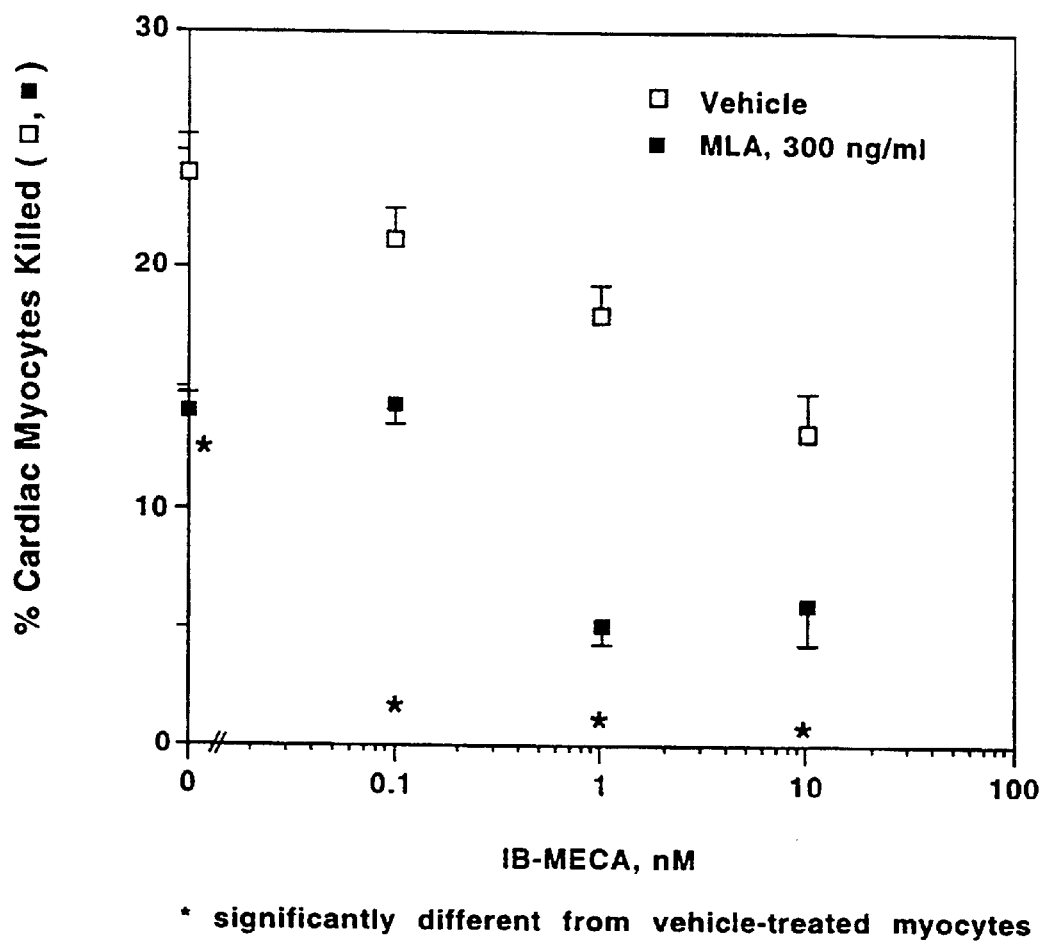
FIG. 7 is a graph showing that pretreatment with MLA enhances the cardioprotective effect of the $A_3$ adenosine receptor agonist, $N^6$-(3-iodobenzyl)adenosine-5'-N-methyluronamide (IB-MECA), during prolonged ischemia (□, vehicle; ■, MLA 300 ng/ml).

Similar results were obtained when cells were pretreated with MLA then treated with IB-MECA, an $A_3$ adenosine receptor agonist during the 90 minute ischemia as described above for FIG. 6. See FIG. 7. Again the results showed a synergistic cardioprotective effect mediated by the combination of the two agents.

Figure 8:
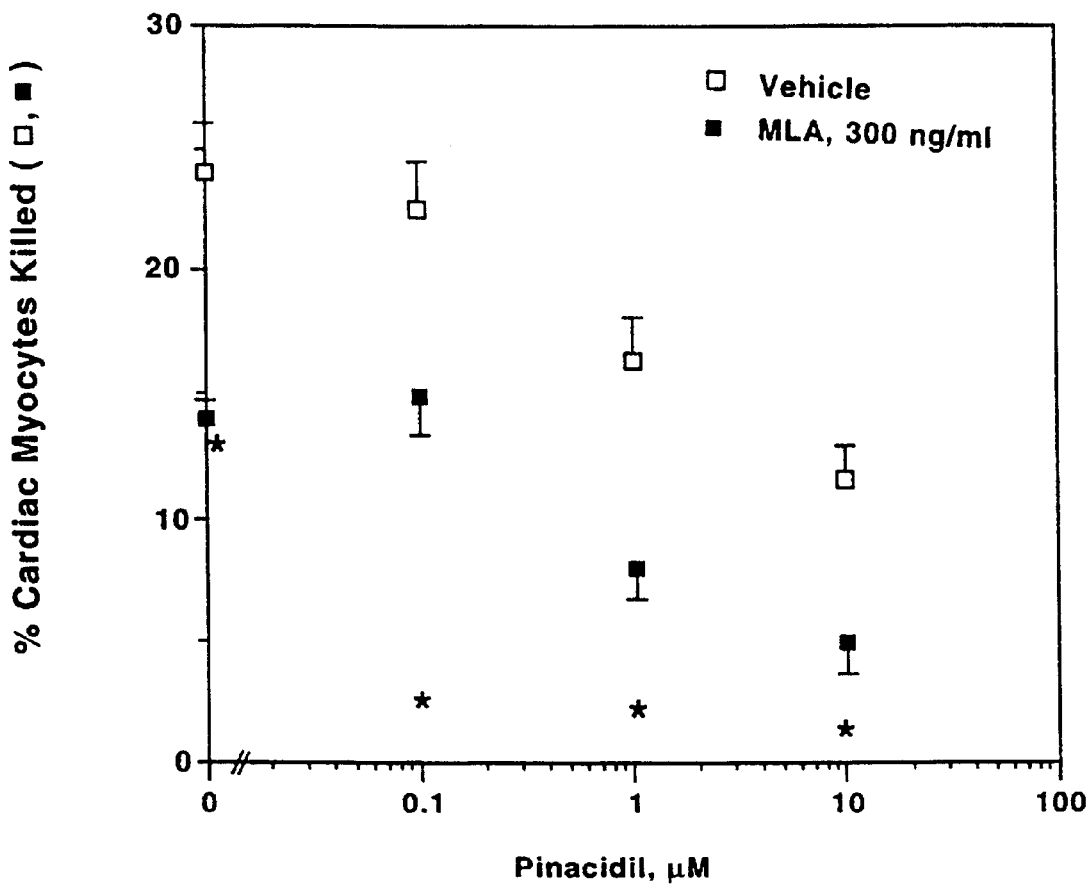
FIG. 8 is a graph showing that pretreatment with increasing concentrations of MLA enhances the cardioprotective effect of pinacidil during prolonged ischemia (□, vehicle; ■, MLA 300 ng/ml).

FIG. 8 shows the results obtained by pretreatment with MLA followed 24 hours later, by exposure to pinacidil, a $K_{ATP}$ channel opener, during the 90 minute ischemia. In MLA-pretreated myocytes, pinacidil caused a greater reduction in the number of cells killed as compared to vehicle pretreatment.

Additional experiments were performed to assess the differences in cardioprotection observed when MLA was administered as the second cardioprotective agent and an adenosine agonist, KATP channel opener or protein kinase C activator was administered as the first cardioprotective agent. The experiments were performed as follows: Cardiac myocytes were exposed to the first cardioprotective agent for 5 minutes and the agent was removed. Cells were then exposed to a period of simulated ischemia in the presence or absence of 300 ng/ml of MLA. The percentage of cells killed by simulated ischemia alone was 27±2% (n=9) in the absence of any treatment with any cardioprotective agent. When MLA was present during the simulated ischemia, the percentage of cells killed was reduced from 27±2% to 14±1.2%. When cells were exposed to 5 minutes of 10 μM pinacidil, a KATP channel opener followed by exposure to simulated ischemia (in the absence of MLA), the percentage of cells killed was 12.3±1. When the pinacidil-treated cells were exposed to simulated ischemia in the presence of MLA, the percentage of cells killed was reduced from 12.3±1% to 6.3±1.2% (n=3). When cells were exposed to 5 minutes of 1 μM PMA, a PKC activator, followed by exposure to simulated ischemia (in the absence of MLA), the percentage of cells killed was 14±1. When PMA-treated cells were then exposed to simulated ischemia in the presence of MLA, the percentage of cells killed was reduced to 10.5±1 (n=3). When cells were exposed to 5 minutes of 10 μM adenosine, followed by exposure to simulated ischemia (in the absence of MLA), the percentage of cells killed was 12±1.4%. When adenosine treated cells were then exposed to simulated ischemia, in the presence of MLA, the percentage of cells killed was reduced to 7.4±1.2% These results indicate that the cardioprotective agents of the invention are effective in reducing ischemic damage of the heart regardless of the order in which they are administered to cells.

The data presented in the Figures illustrate the synergistic effects mediated by the combination of MLA, adenosine receptor agonists and $K_{ATP}$ channel openers in mediating cardioprotection. Accordingly, other agents known to act on the adenosine receptors are contemplated for use in the present invention. Earlier studies have revealed that antagonists at the $A_{2a}$ receptor mediate cardioprotecctive effects. Thus, the combined use of MLA or analogs thereof followed by treatment with an $A_{2a}$ antagonist should also prove to be efficacious in reducing ischemic injury of the heart. Candidate compounds of the following formula that bind and inhibit adenosine $A_{2a}$ receptor activation are set forth below in Table I.

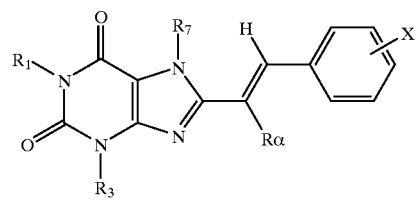

R1, R3=methyl, ethyl, propyl, allyl
R7=H, alkyl (C1–C8)
Rα=H

TABLE I

Affinities of 8 Styrylxanthine Derivatives in Radioligand Binding Assays at Rat Brain $A_1$ and $A_2$-Receptors (47)

| cmpd | $R_1 + R_3$ | $R_1$ | X | $A_1/A_2$ ratio |
|---|---|---|---|---|
| 15b | Me | Me | H | 41 |
| 17b | Me | Me | 2-MeO | 18 |
| 19b | Me | Me | 3-MeO | 64 |
| 20b | Me | Me | 3-$CF_3$ | 25 |
| 21b | Me | Me | 3-$NO_2$ | 11 |
| 22b | Me | Me | 3-$NH_2$ | 30 |
| 23 | Me | Me | 3-(AcNH) | 240 |
| 24 | Me | Me | 3-(HOOC($CH_2)_2$CONH) | 250 |
| 25 | Me | Me | 3-(t-BOC-NH) | 30 |
| 26 | Me | Me | 3-(t-BOC$)_2$N] | 15 |
| 27b | Me | Me | 3-F | 190 |
| 28 | Me | Me | 3-Cl | 520 |
| 29b | Me | Me | 4-MeO | 44 |
| 32b | Me | Me | 3,4-(MeO$)_2$ | 70 |
| 33a | Me | H | 3,5-(MeO$)_2$ | 25 |
| 33b | Me | Me | 3,5-(MeO$)_2$ | >200 |
| 34b | Me | Me | 3,5-$F_2$ | 230 |
| 35 | Me | Me | 3,5-(MeO$)_2$-4-OH | 19 |
| 36 | Me | Me | 4-AcO-3,5-(MeO$)_2$ | 93 |
| 37 | Me | Me | 4-(4-PhCH$_2$O)-3,5-(MeO$)_2$ | 30 |
| 38 | Me | Me | 4-(4-$NH_2$-BuO)-3,5 (MeO$)_2$ | 36 |
| 39 | Me | Me | 4-[4-(tBOC-NH)BuO]-3,5-(MeO$)_2$ | 42 |
| 40 | Me | Me | 4-(4-$NH_2$-trans-$CH_2$CH= $CHCH_2$O-3,5-(MeO$)_2$ | 28 |
| 41 | Me | Me | 4-(4-AcNH-trans-$CH_2$CH= $CHCH_2$O-3,5-(MeO$)_2$ | >50 |
| 42 | Me | Me | 4-(4-t-BOC-NH-trans-$CH_2$CH= $CHCH_2$O-3,5-(MeO$)_2$ | >40 |
| 43b | Me | Me | 2,3,4-(MeO$)_3$ | 34 |
| 44b | Me | Me | 3,4,5-(MeO$)_3$ | 70 [>5600] |
| 45b | Et | Me | 3,4,5-(MeO$)_3$ | 34 |
| 46 | allyl | Me | 3,4,5-(MeO$)_3$ | 13 [>6700] |
| 51b | Pr | Me | 3-Cl | 14 |
| 52b | Pr | Me | 3,4-(MeO$)_2$ | 19 [190] |
| 53b | Pr | Me | 3,5-(MeO$)_2$ | 110 |

Additional compounds contemplated for use as $A_{2a}$ antagonists include:

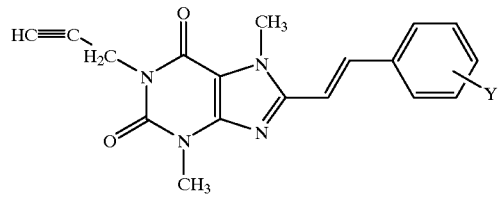

Y=m-Br or p-SO$_3$H (DMPX derivative)

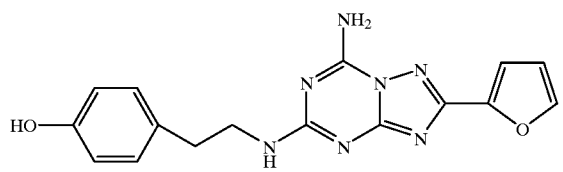

(ZM241385)

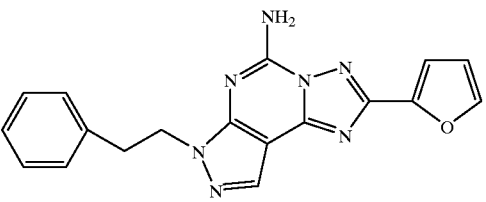

(SCH58261)

As mentioned previously, agonists at the $A_1$ and $A_3$ adenosine receptors are also contemplated for use in the methods of the present invention. Suitable agonists of the following formula are set forth below in Table II.

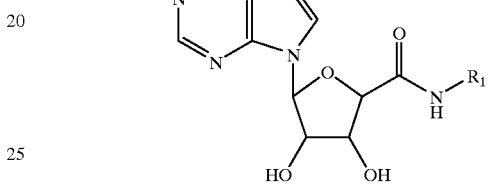

| COMPOUND (Reference) | R$_1$ | R | A$_1$ (nm) | A$_{2a}$ (nm) | A$_3$ (nm) |
|---|---|---|---|---|---|
| Compound 4q (Reference 27) | Ethyl | *(N-(3-iodophenyl)acetamide group)* | 16 | 3940 | 30 |
| Compound 4d (Reference 27) | Ethyl | *(N-(2-trifluoromethylphenyl)acetamide group)* | 384 | >10,000 | 54 |
| Compound 37 (Reference 8) | Ethyl | *(4-nitrophenethyl group)* | 49 | 574 | 9.0 |
| Compound 11 (Reference 28) | Methyl | *(methoxyphenyl group)* | 2060 | 66,300 | 1340 |
| N$^6$-cyclohexyl NECA (Reference 29) | Ethyl | *(cyclohexyl group)* | 0.43 | 170 | 16 |

4q=N⁶-((3-iodophenyl)carbamoyl)adenosine-5'uronamide

4d=N⁶-((2-trifluoromethyl)carbamoyl)adenosine-5'uronamide compound 37=N⁶-(4-Nitrobenzyl)adenosine-5'-N-methyluronamide compound 11=6-(O-Phenylhydroxylamino)purine-9-beta-ribofuranoside-5'-N-methyluronamide N6-cyclohexyl NECA=N6-cyclohexyl 5'-N-ethylcarboxamidoadenosine

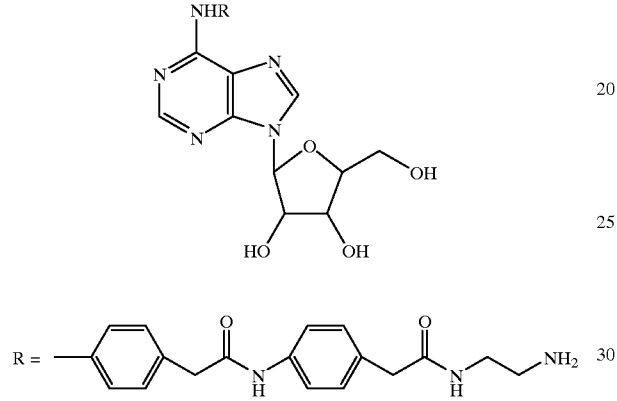

| COMPOUND | R | $A_1$ (nm) | $A_2$ (nm) | $A_3$ (nm) |
|---|---|---|---|---|
| Compound 8* | (See immediately above.) | 0.85 | 210 | 4 |

*N⁶-[4-[[[4-[2-aminoethyl)amino]carbonyl]methyl]anilino]carbonyl]methyl]phenyl]adenosine Other effective A3 agonists suitable for use in practicing the methods of the present invention are set forth below:

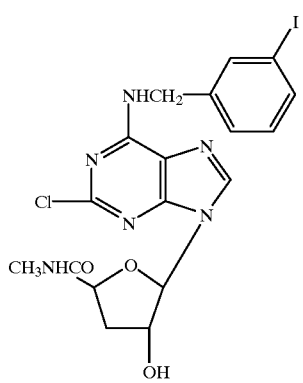

MRS 584

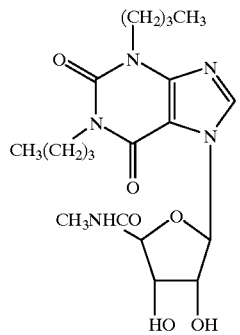

MRS 479 (48)

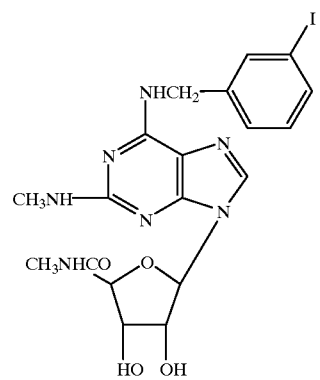

MRS 537 (13)

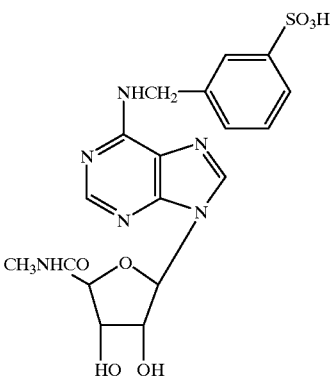

MRS 1340 (8)

EXAMPLE IV

The synergistic cardioprotective effect of MLA used in combination with $A_3/A_1$ agonists and a $K_{ATP}$ channel opener has been demonstrated herein. Combinations of these agents may be used therapeutically in patients who suffer from ischemic damage due to stable angina, unstable angina or post-myocardial infarction angina.

Several administration modalities may be utilized to treat patients with the agents of the invention. These modalities are influenced by bioavailability factors. For example, if the compound is metabolized in the liver or excreted in the bile, some of the active compound absorbed from the gastrointestinal tract will be inactivated by the liver before it can reach the general circulation and for distribution to the site of action. It is not believed that adenosine $A_1/A_3$ receptor agonists, adenosine $A_{2a}$, receptor antagonists or $K_{ATP}$ will be subject to this first pass loss. Additionally, because the agonists of the invention are polar and water soluble, it is expected that they will have a small volume of distribution, and thus be readily eliminated by the kidney. Moreover, binding of these agents to plasma proteins may limit their free concentrations in tissues and at their locus of action since it is only the unbound drug which equilibrates across membrane receptor sites.

Another factor affecting bioavailability is the distribution of the agonists to tissues. Given the relatively small size of these compounds and their water solubility, it is anticipated that the compounds will have a relatively fast second phase of drug distribution. This distribution is determined by both the blood flow to the particular tissue of the organ such as the heart, as well as the rate at which the compounds diffuse into the interstitial compartment from the general circulation through the highly permeable capillary endothelium.

MLA or synthetic analogs thereof are lipophilic and will be administered intravenously in a 10% ethanol, 40% propylene glycol water solution. Alternatively MLA or its analogs can be given orally in capsules or tablets. MLA or its analogs would be administered in doses ranging from 1–20 μg/kg body weight. Patients may be perfused with the adenosine receptor $A_1$ or $A_3$ agonists, adenosine $A_{2a}$ receptor antagonists or $K_{ATP}$ channel openers of the invention by dissolving them in normal saline solution or using emulsifying agents or cosolvents followed by intravenous administration every four to six hours. Effective doses usually range from 100 to 300 nM. For example, considering a 15 liter volume of distribution for a 70 kg patient, a loading dose ranging from 0.5 to 1.5 mg is preferably used. Depending on the half-life of the agonists in the body, several doses, e.g., 1.5–4.5 mg may be administered per day.

Alternatively, a time-release or slow-release preparation may be utilized which allows for periodic or constant release of the agonists, antagonists or channel openers over a given time period. This method would allow for a single dose of these agents in a given day. Methods for preparing such capsules are well known to those of skill in the art of drug delivery.

While the combined use of MLA with specific $A_3$ and $A_1$ agonists or $K_{ATP}$ channel openers has been exemplified herein, other compounds have been identified which have high affinity for both the $A_3$ and $A_1$ receptor, also other compounds are known to those skilled in the art that function to open the $K_{ATP}$ channel. Additionally, analogs or derivatives of MLA are known. Any of these compounds or agents therefore may also be used in the practice of the instant invention.

REFERENCES

1. Babbitt, D. G., R. Virmani, and M. B. Forman. Intracoronary adenosine administered after reperfusion limits vascular injury after prolonged ischemia in the canine model. Circ. 80:1388–1399, 1989.
2. Belardinelli, L. B., J. Linden, and R. M. Berne. The cardiac effects of adenosine Prog. Cardiovasc. Dis. 32:93–97, 1989.
3. Carr, C. S., R. J. Hill, H. Masamune, S. P. Kennedy, D. R. Knight, W. R. Tracey, and D. M. Yellon. A role for adenosine $A_3$ receptors in ischemic preconditioning in the human atrium. Circ 94 (8):3220, 1996.
4. Deutsch, E., M. Berger, W. G. Kussmaul, J. W. Hirshfield, H. C. Hermann, and W. K. Laskey. Adaptation to ischemia during percutaneous transluminal coronary angioplasty: Clinical, hemodynamic, and metabolic features. Circ. 82:2044–2051, 1990.
5. Downey, J. M. Ischemic preconditioning. Nature's own cardioprotective intervention. Trends Cardiovasc. Med. 2:170–176, 1992.
6. Ely, S. W., R. M. Mentzer, R. D. Lasley, B. K. Lee, and R. M. Berne. Functional and metabolic evidence of enhanced myocardial tolerance to ischemia and reperfusion with adenosine. J. Thorac. Cardiovasc. Surg. 90:549–556, 1985.
7. Ely, S. W. and R. M. Berne. Protective effects of adenosine in myocardial ischemia. Circulation 85:893–904, 1992.
8. Gallo-Rodriguez, C., X. Ji, N. Melman, B. D. Siegman, L. H. Sanders, J. Orlina, B. Fischer, Q. Pu, M. E. Olah, P. J. M. Van Galen, G. L. Stiles, and K. A. Jacobson. Structure-activity relationships of N6-benzyladenosine-5'-uronamides as $A_3$-selective adenosine agonists. J. Med. Chem. 37:636–646, 1994.
9. Gross, G. J. ATP-sensitive potassium channels and myocardial preconditioning. Basic Res. Cardiol. 90:85–88, 1995.
10. Hill, R. J., J. J. Oleynek, M. A. Ravi Kiron, H. Masamune, W. Weng, R. A. Buchholz, D. Knight, W. R. Tracey, R. T. Wester, and S. P. Kennedy. Cloning, expression, and pharmacological characterization of rabbit adenosine $A_1$ and $A_3$ receptors. J. Pharmacol. Exp. Ther. 280:122–128, 1997.
11. Jacobson, K. A., K. L. Kirk, W. L. Padget, and J. W. Daly. Functionalized congeners of adenosine: preparation of analogues with high affinity for $A_1$-adenosine receptors. J. Med,.Chem. 28:1341–1346, 1985.
12. Jiang, J. -L., A. M. van Rhee, N. Melman, X. D. Ji, and Jacobson, K. A. 6-phenyl-1,4-dihydropyridine derivatives as potent and selective $A_3$ adenosine receptor antagonists. J. Med. Chem. 39:4667–4675, 1996.
13. Kim, H. O., X. Ji, S. M. Siddiqi, M. E. Olah, G. L. Stiles, and K. A. Jacobson. 2-Substitution of N6-benzyladenosine-5'-uronamides enhances selectivity for $A_3$ adenosine receptors. J. Med. Chem. 37:3614–3621, 1994.
14. Li, G. C., J. A. Vasquez, K. P. Gallagher, and B. R. Lucchesi. Myocardial protection with preconditioning. Circ. 82:609–619, 1990.
15. Liang, B. T. Adenosine receptors and cardiovascular function. Trends in Cardiovascular Medicine 2:100–108, 1992.
16. Liang, B. T. Direct preconditioning of cardiac ventricular myocytes via adenosine $A_1$ receptor and $K_{ATP}$ channel. Am. J. Physiol. 271:H1769-H1777, 1996.
17. Miura, T., T. Ogawa, T. Iwamoto, K. Shimamoto, and O. Iimura. Dipyridamole potentiates the myocardial infarct size-limiting effect of ischemic preconditioning. Circ. 86:979–985, 1992.
18. Murry, C. E., R. B. Jennings, and K. A. Reimer. Preconditioning with ischemia: A delay of lethal cell injury in ischemic myocardium. Circ. 74:1124–1136, 1986.
19. Olafsson, B., M. B. Forman, D. W. Puett, A. Pou, C. U. Cates. Reduction of reperfusion injury in the canine preparation by intracoronary adenosine: Importance of the endothelium and the no-reflow phenomenon. Circ. 76:1135–1145, 1987.
20. Olsson, R. A. and J. D. Pearson. Cardiovascular purinoceptors. Physiol. Rev. 70:761–809, 1990.
21. Reibel, D. K., and M. J. Rovetto. Myocardial ATP synthesis and mechanical function following oxygen deficiency. Am. J. Physiol. 234:H620–H624, 1978.

22. Reibel, D. K. and M. J. Rovetto. Myocardial adenosine salvage rates and restoration of ATP content following ischemia. Am. J. Physiol. 237:H247–H252, 1979.
23. Strickler, J., K. A. Jacobson, and B. T. Liang. Direct preconditioning of cultured chick ventricular myocytes: Novel functions of cardiac adenosine $A_{2a}$ and $A_3$ receptors. J. Clin. Invest. 98:1773–1779, 1996.
24. Tracey, W. R., R. J. Hill, A. H. Smith, F. W. Bangerter, J. T. McAndrew, S. P. Kennedy, H. Masamune, R. T. Wester, and R. A. Buchholz. Selective adenosine $A_3$ receptor stimulation reduces ischemic myocardial injury in the rabbit heart. Circ. 94:3218–?, 1996.
25. Wyatt, D. A., S. W. Ely, R. D. Lasley, R. Walsh, R. Mainwaring, R. M. Berne, and R. M. Mentzer. Purine-enriched asanguineous cardioplegia retards adenosine triphosphate degradation during ischemia and improves post ischemic ventricular function. J. Thorac. Cardiovasc. Surg. 97:771–778, 1989.
26. Zhou, Q. Y., C. Li, M. E. Olah, R. A. Johnson, G. L. Stiles, and O. Civelli. Molecular cloning and characterization of an adenosine receptor: The $A_3$ adenosine receptor. Proc. Natl. Acad. Sci. USA 89:7432–7436, 1992.
27. Baraldi, P. G., B. Cacciari, G. Spalluto, X. Ji, M. E. Olah, G. Stiles, S. Dionisotti, C. Zocchi, E. Ongini, and K. Jacobson. Novel N6-(substituted-phenylcarbamoyl) adenosine-5'uronamides as potent agonists for $A_3$ adenosine receptors. J. Med. Chem. 39:802–806, 1996.
28. Siddiqi, S. M., R. A. Pearlstein, L. H. Sanders, and K. A. Jacobson. Comparative molecular field analysis of selective $A_3$ adenosine receptor agonists. Bioorg. Med. Chem. 3:1331–1343, 1995.
29. Van Galen, P. J. M., A. H. Van Bergen, C. Gallo-Rodriguez, N. Melman, M. E. Olah, A. P. IJzerman, G. L. Stiles, and K. A. Jacobson. A binding site model and structure-activity relationships for the rat $A_3$ adenosine receptor. Mol. Pharmacol. 5:1101–1111, 1994.
30. Jacobson, K. A., K. L. Kirk, W. L. Padgett, and J. W. Daly. Functionalized cogeners of adenosine: Preparation of analogues with high affinity for $A_1$-adenosine receptors. J. Med. Chem. 28:1341–1346, 1985.
31. Elliott, G. T. Pharmacologic myocardial predonditioning with monophosphoryl lipid A (MLA) reduces infarct size and stunning in dogs and rabbits. Ann. N. Y. Acad. Sci. 793:386–399, 1996.
32. Stambaugh, K., J. -L. Jiang, K. A. Jacobson, and B. T. Liang. Novel cardioprotective function of adensosine $A_3$ receptor during prolonged simulated ischemia. Am. J. Physiol. 273:H501–H505, 1997.
33. DeHaan, R. L. 1967. Developmental changes in the calcium currents in embryonic chick ventricular myocytes. Dev. Biol. 16:216–249.
34. Galper, J. B., and T. W. Smith. 1978. Properties of muscarinic acetylcholine receptors in heart cell cultures. Proc. Natl. Acad. Sci. U.S.A. 75: 5831–5835.
35. Barry, W. H., and T. W. Smith. 1982. Mechanisms of transmembrane calcium movement in cultured chick embryo ventricular cells. J. Physiol. 325:243–260.
36. Marsh, J. D., D. Lachance, and D. Kim. 1985. Mechanism of b-adrenergic receptor regulation in cultured chick heart cells. Circ. Res. 57:171–181.
37. Liang, B. T., M. R. Hellmich, E. J. Neer, and J. B. Galper. 1986. Development of muscarinic cholinergic inhibition of adenylate cyclase in embryonic chick hearts: its relationship to changes in the inhibitory guanine nucleotide regulatory protein. J. Biol. Chem. 261:9011–9021.
38. Stimers, J. R., S. Liu, and M. J. Lieberman. 1991. Apparent affinity of the Na/K pump for ouabain in cultured chick cardiac myocytes. J. Gen. Physiol. 98: 815–833.
39. Xu, H., J. Miller, and B. T. Liang. 1992. High-efficiency gene transfer into cardiac myocytes. Nucleic Acids Res. 20:6425–6426.
40. Jacobson, K. A., O. Nikodijevic, W. L. Padgett, C. Gallo-Rodriguez, M. Maillard, and J. W. Daly. 1993. 8-(3-chlorostyryl)caffeine is a selective A2-adenosine antagonist in vitro and in vivo. Fed. Eur. Biochem. Soc. 323: 141–144.
41. Gallo-Rodriguez, C., X. Ji, N. Melman, B. D. Siegman, L. H. Sander, J. Orlina, B. Fischer, Q. Pu, M. E. Olah, P. J. M. Van Galen, G. L. Stiles, K. A. Jacobson. 1994. Structure-activity relationships of N6-benzyladenosine-5'-uronamides as $A_3$-selective adenosine agonists. J. Med. Chem. 37:636–646.
42. Kim, H. O., X. Ji, S. M. Siddiqi, M. E. Olah, G. L. Stiles, K. A. Jacobson. 1994. 2-Substitution of N6-benzyladenosine-5'-uronamides enhances selectivity for $A_3$ adenosine receptors. J. Med. Chem. 37:3614–3621.
43. Brown, J. M., Grosso, M. A., Terada, L. S., Whitman, GJR., Banerjee, A.,White, C. W., Harken, A. H., Repine, J. E. 1989. Endotoxin pretreatment increases endogenous myocardial catalase activity and decreases ischemia-reperfusion injury of isolated rat hearts. Proc. Natl. Acad. Sci. USA 86:2516–2520.
44. Yoshida et al., 1996. Monophosphoryl lipid A induces pharmacologic preconditioning in rabbit hearts without concomitant expression of 70 kDa heat shock protein. Mol. Cell. Biochem. 156:1–8.
45. Yao, et al., (1993) Cardioprotective effects of monophosphoryl lipid A, a novel endotoxin analog, in the dog. Cardiovascular Research 27:832–838.
46. Mestril, K., S-H Chi, M. R. Sayen, K. O'Reilly, W. H. Dillman, (1994) Expression of inducible stress protein 70 in rat heart myogenic cells confers protection against simulated ischemia-induced injury. J. Clinical Invest. 93:759–767.
47. Jacobson, K. A., Gallo-Rodriquez, C., Melman, N., Fischer, B., Maillard, M., van Bergen, A., van Galen, P. J., Karton, Y. Structure-Activity Relationships of 8-Stryrylxanthines as $A_2$-Selective Adenosine Antagonists J. Med. Chem. 36:1333–1342, 1992
48. Jacobson, K. A., Kim, H. O., Siddiqi, S. M., Olah, M. E., Stiles, G., and von Lubitz, D. K. J. E. A3 adenosine receptors: design of selective ligands and therapeutic agents. Drugs of the Future. 20:689–699, 1995.

While certain preferred embodiments of the present invention have been described and specifically exemplified above, it is not intended that the invention be limited to such embodiments. Various modifications may be made to the invention without departing from the scope and spirit thereof as set forth in the following claims.

What is claimed is:

1. A method for preventing or reducing ischemic heart damage, in a patient in need of such treatment, comprising administering to said patient a first cardioprotective agent followed by adminstration of a second cardioprotective agent, said first and second cardioprotective agents acting synergistically to protect the heart from ischemic damage.

2. A method as claimed in claim 1, wherein said first cardioprotective agent is selected from the group consisting of monophosphoryl lipid A, a synthetic analog of monophosphoryl lipid A, adenosine A1 agonists or adenosine A3 agonists.

3. A method as claimed in claim 1, wherein said second cardioprotective agent is selected from the group consisting of adenosine A1 receptor agonists, adenosine A3 receptor agonists, $N^6$-((3-iodophenyl)carbamoyl)adenosine- 5'uronamide, $N^6$-((2-trifluoromethyl)carbamoyl)adenosine-5'uronamide, $N^6$-(4-nitrobenzyl)adenosine-5'-N-methyluronamide, 6-(O-phenylhydroxylamino purine-9-beta-ribofuranoside-5'-N-methyluronamide, $N^6$-cyclohexyl-5'-N-ethylcarboxamido)adensine, $N^6$-[4-[[[4-[2-aminoethyl)amino]carbonyl]methyl]-anilino]carbonyl]methyl]phenyl]adenosine, MRS 584, MRS 479, MRS 537, MRS 1340, adenosine A2a receptor antagonists, 8 styrylxanthine derivative compounds listed in Table I consisting of compounds 15b, 17b, 19b, 20b, 21b, 22b, 23, 24, 25, 26, 27b, 28, 29b, 32b, 33a, 33b, 34b, 35, 36, 37, 38, 39, 40, 41, 42, 43b, 44b, 45b, 46, 51b, 52b, 53b, PKC activators and $K_{ATP}$ channel openers.

4. A method as claimed in claim 1, wherein said first cardioprotective agent is administered to said patient by an administration means selected from the group consisting of intravenous administration, direct cardiac perfusion, or oral administration.

5. A method as claimed in claim 1, wherein said second cardioprotective agent is administered to said patient by an administration means selected from the group consisting of intravenous administration, direct cardiac perfusion, or oral administration.

6. A method as claimed in claim 1, wherein said patient is in need of said treatment due to the presence of angina selected from the group consisting of unstable angina or post-myocardial infarction angina.

7. A method as claimed in claim 1, wherein said cardioprotective agents are admininistered to said patient prior to a surgical procedure which may cause cardiac ischemic damage.

8. A method as claimed in claim 1, wherein said cardioprotective agents are admininistered to said patient during a surgical procedure which may cause cardiac ischemic damage.

9. A method as claimed in claim 1, wherein said cardioprotective agents are admininistered to said patient following a surgical procedure which may cause cardiac ischemic damage.

10. A method for enhancing myocardial responsiveness to preconditioning stimuli in a patient in need of such treatment comprising administering to said patient a first cardioprotective agent followed by adminstration of a second cardioprotective agent, said first and second cardioprotective agents acting synergistically to enhance myocardial responsiveness.

11. A method as claimed in claim 10, wherein said first cardioprotective agent is selected from the group consisting of monophosphoryl lipid A, a synthetic analog of monophosphoryl lipid A, adenosine A1 agonists or adenosine A3 agonists.

12. A method as claimed in claim 10, wherein said second cardioprotective agent is selected from the group consisting of adenosine A1 receptor agonists, adenosine A3 receptor agonists, adenosine A2a receptor antagonists, 8 styrylxanthine derivative compounds listed in Table I consisting of compounds 15b, 17b, 19b, 20b, 21b, 22b, 23, 24, 25, 26, 27b, 28, 29b, 32b, 33a, 33b, 34b, 35, 36, 37, 38, 39, 40, 41, 42, 43b, 44b, 45b, 46, 51b, 52b, 53b, PKC activators and $K_{ATP}$ channel openers.

13. A method as claimed in claim 10, wherein said first cardioprotective agent is administered to said patient by an administration means selected from the group consisting of intravenous administration, direct cardiac perfusion, or oral administration.

14. A method as claimed in claim 10, wherein said second cardioprotective agent is administered to said patient by an administration means selected from the group consisting of intravenous administration, direct cardiac perfusion, or oral administration.

15. A method as claimed in claim 10, wherein said patient is in need of said treatment due to the presence of angina selected from the group consisting of unstable angina or post-myocardial infarction angina.

16. A method as claimed in claim 10, wherein said cardioprotective agents are admininistered to said patient prior to a surgical procedure which may cause cardiac ischemic damage.

17. A method for reducing or preventing ischemic heart damage in a patient in need of such treatment, comprising the administration of first and second cardioprotective agents, said first cardioprotective agent being selected from the group consisting of A1 adenosine agonists or A3 adenosine agonists, $K_{ATP}$ channel openers, and PKC activators followed by the administration of a second cardioprotective agent selected from the group consisting of monophosphoryl lipid A or synthetic analogs of monophosphoryl lipid A.

18. A method as claimed in claim 17, wherein said cardioprotective agents are admininistered to said patient prior to a surgical procedure which may cause cardiac ischemic damage.

19. A method as claimed in claim 17, wherein said cardioprotective agents are admininistered to said patient during a surgical procedure which may cause cardiac ischemic damage.

20. A method as claimed in claim 17, wherein said cardioprotective agents are admininistered to said patient following a surgical procedure which may cause cardiac ischemic damage.

21. A method as claimed in claim 17, wherein said first cardioprotective agent is administered to said patient by an administration means selected from the group consisting of intravenous administration, direct cardiac perfusion, or oral administration.

22. A method as claimed in claim 17, wherein said second cardioprotective agent is administered to said patient by an administration means selected from the group consisting of intravenous administration, direct cardiac perfusion, or oral administration.

23. A method as claimed in claim 17, wherein said patient is in need of said treatment due to the presence of angina selected from the group consisting of unstable angina or post-inyocardial infarction angina.

24. A method as claimed in claim 17, wherein said $K_{ATP}$ channel opener is nicorandil.

25. A method as claimed in claim 17, wherein said first cardioprotective agent is selected from the group consisting of $N^6$-((3-iodophenyl)carbamoyl)adenosine-5'uronamide, $N^6$-((2-trifluoromethyl)carbamoyl)adenosine-5'uronamide, $N^6$-(4-nitrobenzyl)adenosine-5'-N-methyluronamide, 6-(O-phenylhydroxylamino purine-9-beta-ribofuranoside-5'-N-methyluronamide, $N^6$-cyclohexyl-5'-N-ethylcarboxamido)adensine, $N^6$-[4-[[[4-[2-aminoethyl)amino]carbonyl]methyl]-anilino]carbonyl]methyl]phenyl]adenosine, MRS 584, MRS 479, MRS 537, and MRS 1340.

26. A method for enhancing myocardial responsiveness to preconditioning stimuli in a patient in need of such treatment comprising administering to said patient a first cardioprotective agent followed by adminstration of a second cardioprotective agent, said first cardioprotective agent being selected from the group consisting of A1 adenosine agonists or A3 adenosine agonists, $K_{ATP}$ channel openers, and PKC activators followed by the administration of a second cardioprotective agent selected from the group consisting of A2a antagonists, monophosphoryl lipid A or synthetic analogs of monophosphoryl lipid A, said first and second cardioprotective agents acting synergistically to enhance myocardial responsiveness.

27. A method as claimed in claim 26, wherein said first cardioprotective agent is administered to said patient by an administration means selected from the group consisting of intravenous administration, direct cardiac perfusion, or oral administration.

28. A method as claimed in claim 26, wherein said second cardioprotective agent is administered to said patient by an administration means selected from the group consisting of intravenous administration, direct cardiac perfusion, or oral administration.

29. A method as claimed in claim 26, wherein said patient is in need of said treatment due to the presence of angina selected from the group consisting of unstable angina or post-myocardial infarction angina.

30. A method as claimed in claim 26, wherein said cardioprotective agents are admininistered to said patient prior to a surgical procedure which may cause cardiac ischemic damage.

* * * * *